(12) United States Patent
Allen et al.

(10) Patent No.: US 8,810,638 B2
(45) Date of Patent: Aug. 19, 2014

(54) INSERTABLE SURGICAL IMAGING DEVICE

(75) Inventors: Peter K. Allen, Pleasantville, NY (US); Dennis L. Fowler, Boston, MA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 395 days.

(21) Appl. No.: 12/770,246

(22) Filed: Apr. 29, 2010

(65) Prior Publication Data

US 2010/0245549 A1    Sep. 30, 2010

Related U.S. Application Data

(63) Continuation-in-part of application No. PCT/US2008/012347, filed on Oct. 31, 2008.

(60) Provisional application No. 61/001,531, filed on Nov. 2, 2007, provisional application No. 61/054,282, filed on May 19, 2008.

(51) Int. Cl.
*A62B 1/04* (2006.01)
*H04N 7/18* (2006.01)

(52) U.S. Cl.
USPC ................................... 348/65; 348/E07.001

(58) Field of Classification Search
CPC .. H04N 2005/2255; H04N 7/183; A61B 1/05; A61B 1/042; A61B 1/045
USPC .......................................... 348/65; 600/476
See application file for complete search history.

(56) References Cited

U.S. PATENT DOCUMENTS

| 5,606,458 | A | 2/1997 | Fergason |
| 5,870,188 | A | 2/1999 | Ozaki et al. |
| 6,127,784 | A | 10/2000 | Grossman et al. |
| 6,277,064 | B1 | 8/2001 | Yoon |
| 7,066,879 | B2 | 6/2006 | Fowler et al. |
| 7,413,543 | B2 * | 8/2008 | Banik et al. ................... 600/129 |
| 7,751,870 | B2 * | 7/2010 | Whitman ...................... 600/476 |
| 8,229,549 | B2 * | 7/2012 | Whitman et al. ............. 600/478 |
| 2002/0049596 | A1 * | 4/2002 | Burchard et al. ............. 704/270 |

(Continued)

FOREIGN PATENT DOCUMENTS

| EP | 1759629 A1 | 3/2007 |
| WO | WO-2009058350 A1 | 5/2009 |

OTHER PUBLICATIONS

"International Application Serial No. PCT/US2008/012347, International Search Report mailed Jan. 6, 2009", 08 pgs.

(Continued)

*Primary Examiner* — Dave Czekaj
*Assistant Examiner* — Nam Pham
(74) *Attorney, Agent, or Firm* — Schwegman Lundberg & Woessner, P.A.

(57) ABSTRACT

A body-insertable imaging device includes a first camera that comprises a first image sensor and a first lens to pass incident light onto the first image sensor, a control interface to receive a remotely generated control signal, and an actuator communicatively coupled to the control interface and configured to support the camera and manipulate the camera about a pan axis, a tilt axis, and along a zoom direction in response to the control signal while the camera and actuator are within a body cavity, wherein the zoom direction extends out from a distal end of the body-insertable camera.

27 Claims, 5 Drawing Sheets

(56) References Cited

U.S. PATENT DOCUMENTS

| | | |
|---|---|---|
| 2005/0177026 A1 | 8/2005 | Hoeg et al. |
| 2006/0198619 A1* | 9/2006 | Oleynikov et al. ............. 396/14 |
| 2007/0023477 A1* | 2/2007 | Whitman et al. .......... 227/175.1 |
| 2007/0032701 A1* | 2/2007 | Fowler et al. ................. 600/173 |

OTHER PUBLICATIONS

"International Application Serial No. PCT/US2008/012347, Written Opinion mailed Jan. 6, 2009", 08 pgs.

"European Application Serial No. 08843342.0, Extended European Search Report mailed Mar. 25, 2011", 8 pgs.

"European Application Serial No. 08843342.0, Communication mailed Apr. 12, 2011", 1 pg.

"European Application Serial No. 08843342.0, Office Action mailed Dec. 20, 2011", 5 pgs.

"European Application Serial No. 08843342.0, Response filed Apr. 30, 2012 to Office Action mailed Dec. 20, 2011", 12 pgs.

"European Application Serial No. 08843342.0, Response filed Oct. 24, 2011 to Communication mailed Apr. 12, 2011", 19 pgs.

"International Application Serial No. PCT/US2008/012347, International Preliminary Report on Patentability dated May 4, 2010", 7 pgs.

* cited by examiner

INSERTABLE SURGICAL IMAGING DEVICE

CLAIM OF PRIORITY

This patent application is a continuation-in-part of PCT Application PCT/US2008/012347, filed Oct. 31, 2008, published as WO 2009/058350 A1 on May 7, 2009, which claims the benefit of priority under 35 U.S.C. §119(e) to U.S. Provisional Application Ser. No. 61/001,531, filed on Nov. 2, 2007, and to U.S. Provisional Application Ser. No. 61/054,282 filed on May 19, 2008, which are herein incorporated by reference in their entirety, the benefit of priority of each of which is claimed herein.

STATEMENT REGARDING FEDERALLY FUNDED RESEARCH

This invention is made with government support under NIH grant 1R21EB004999-01A1 awarded by the NIH. The government has certain rights in the invention.

BACKGROUND

Imaging can be used during surgery, including in the field of Minimally Invasive Surgery (MIS). "Minimally invasive" does not refer to the least invasive technique possible, but instead refers to techniques that are less invasive than conventional open surgery.

OVERVIEW

The present inventors have recognized that, in MIS, surgeons are typically constrained by the use of a standard endoscope. Standard endoscopes suffer from the paradigm of pushing long sticks into small openings which is quite limiting. The present inventors have recognized that this approach has a number of problems including a narrow imaging field of view, limited work space, counter intuitive motions required by the operator or user, and multiple incisions for the endoscope ports and effector tooling.

In laparoscopic surgery, the surgeon first cuts several small incisions in the abdomen, and inserts trocars (small tubes) through the incisions. Carbon dioxide gas can be pumped into the abdomen to create a larger volume of space for the operation and visualization. However, the present inventors have recognized that laparoscopy can drastically increase the complexity of a surgeon's task because of the rigid, stick-like instruments, impaired depth perception, loss of touch (haptics), and the difficulty in varying the perspective view of the operative field. The present inventors have recognized value in enhancing and improving imaging related to surgical procedures.

Accordingly, this document relates generally to imaging systems and imaging devices used for surgical procedures. An example of an imaging device can comprise an implantable camera that can include a first image sensor, a first lens to pass incident light onto the first image sensor, a control interface to receive a remotely generated control signal, and an actuator communicatively coupled to the control interface and configured to support the camera and manipulate the camera about a pan axis, a tilt axis, and along a zoom direction in response to the control signal while the camera and actuator are within a body cavity.

Another example of an imaging device can comprise a light source, an implantable stereo camera, a control interface to receive a remotely generated control signal, and an actuator communicatively coupled to the control interface and configured to support the camera and manipulate the camera about a pan axis and a tilt axis in response to the control signal while the camera and actuator are within a body cavity. The stereo camera can include a first image sensor and a second image sensor within an implantable housing, a first lens to pass incident light onto the first image sensor, and a second lens to pass incident light onto the second image sensor. The first and second image sensors can be configured to independently provide image data to an external device for constructing a three-dimension (3D) image.

An example of an imaging system can comprise an implantable imaging device and a remote control device. The implantable imaging device can include a light source, a first camera that includes a first image sensor and a first lens to pass incident light onto the first image sensor, a first control interface, a first control interface to receive a remotely generated control signal, and an actuator configured to support the camera and manipulate the camera about a pan axis, a tilt axis, and along a zoom direction in response to the control signal while the camera and actuator are within a body cavity. The remote control device can include a processor configured to receive image data from the implantable imaging device, and a second control interface communicatively coupled to the processor. The processor can be communicatively coupled to a motion control module configured to generate the control signal in response to input received via the second control interface.

This section is intended to provide an overview of subject matter of the present patent application. It is not intended to provide an exclusive or exhaustive explanation of the invention. The detailed description is included to provide further information about the present patent application.

DETAILED DESCRIPTION

The present patent application discusses, among other things, systems and methods to enhance and improve surgical procedures, such as by placing inside the body one or more small, mobile, multi-function platforms that can begin to assume some of the tasks associated with surgery. An imaging system can include a single port surgical system, in which a single access port can be used to introduce multiple sensors and effectors into the body cavity. Imaging is used herein to generally denote relating to reproducing an image of a site, such as producing a video image of a surgical site for example. One or more imaging devices, such as an imaging robot, can be remotized and controlled inside the body, such as by using one or more visual and haptic interfaces. A feedback loop can be created, such as by using insertable sensor technology and one or more effectors, with both a surgeon and a computer in the information-processing/control loop.

The benefits of a robotic approach can include greater precision, less trauma to the patient, and improved surgical outcome. The imaging devices are insertable anywhere in the body and can be used for a number of surgical procedures including, among other things, an appendectomy, a nephrectomy, measuring the bowel, and suturing.

Figure 1:
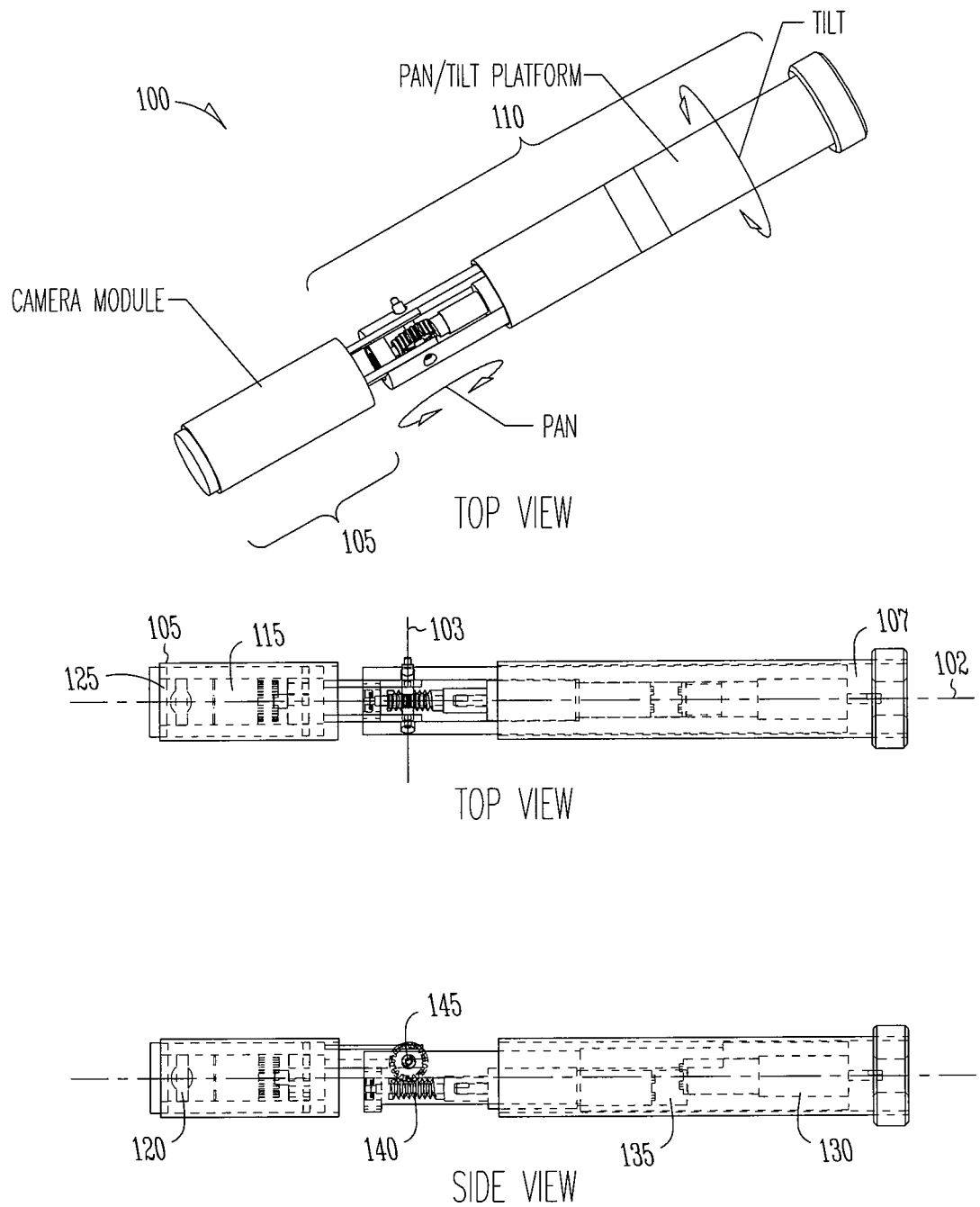
FIG. 1 shows drawings of an example of a body-insertable surgical imaging device.

FIG. 1 shows an example of a body-insertable surgical imaging device 100. The design of the imaging device 100 can be modular, such as to make the components interchangeable and extendable. The imaging device 100 can include an implantable camera 105 or camera module, a control interface 107, and an actuator 110. The implantable camera 105 can include a first image sensor 115, such as a charge coupled device (CCD) sensor or CMOS sensor for example, and a first lens 120 to pass incident light onto the first image sensor 115. In certain examples, the first image sensor 115 can include a CCD chip having a very small package size (e.g., 0.25 in.). In certain examples, the lens can include a miniature pin-hole lens (e.g., F no. 5.0).

The actuator 110 can support the camera module and can manipulate the camera module about a pan axis, a tilt axis, and along a zoom direction. The control interface 107 can receive a remotely generated control signal. The actuator 110 can manipulate the camera in response to the control signal, such as while the camera 105 and actuator 110 are within a body cavity. In some examples, the control interface 107 can receive a sequence current appropriate to drive the actuator. The electrical connection to the imaging device can include one or more wires or cables having a smaller diameter than the housing of the actuator. This allows the imaging device 100 to be inserted via a single access port into the patient, such as via a trocar.

In some examples, the control interface includes a radio frequency (RF) receiver or transceiver circuit. The control interface may be a wireless interface that receives a remotely generated wireless control signal. In some examples, the power source for the imaging device is separate from the controller. This allows the imaging device to be physically decoupled from a controlling device and eliminates the need for wires or cables.

The imaging device 100 has a body-insertable or implantable housing. The housing is implantable because it is made from biocompatible material that is inert to body fluid and tissue. In some examples, the implantable housing of the imaging device 100 can include a shell of stainless steel, plastic, or other implantable material, to house the imaging device 100. The housing can have a housing diameter receivable by a trocar, such as a trocar having a trocar diameter less than or equal to twelve millimeters (12 mm). This allows the imaging device 100 to be insertable into a patient's body via a trocar of standard size. In some examples, the implantable housing includes one or more magnetic pads, such as on one or more of the ends of the imaging device 100. When the imaging device 100 is fully deployed into the abdomen of the patient, the user can use one or more external magnetic components, such as to fix the imaging device 100 or to also maneuver the locomotion of the imaging device 100 in the body using control from outside the body.

In some examples, the actuator 110 can include a separate pan mechanism, tilt mechanism, and zoom mechanism. The tilt axis is in the direction of the elongated axis 102 of the imaging device 100. The tilt mechanism rotates the implantable camera 105 about the elongated axis 102. In some examples, the tilt mechanism can include a tilt actuator such as a tilt motor 130 to move the implantable camera 105 in a tilt direction about the tilt axis. In certain examples, the tilt motor 130 can include a DC brushless motor. The shaft of the tilt motor 130 can be coupled to the implantable housing, such as an external stainless steel shell, that houses the actuator 110. The implantable housing can be used as a base to mount the imaging device 100 to the wall of a body cavity.

The pan axis is in the direction of an axis 103 orthogonal to the imaging device 100. The pan mechanism rotates the implantable camera about the pan axis. In some examples, the pan mechanism can include a worm gear mechanism such as having a worm 140 and worm gear 145, and a pan actuator to engage and drive the worm gear 145. In some examples, the pan actuator can include a pan motor 135 similar to the tilt motor 130. The worm gear mechanism can be useful for providing transverse motion with increased output torque in a small space. In some examples, the worm gear 145 can have a reduction ratio of 16:1. In certain examples, the tilt mechanism provides a tilt range of over ninety degrees and the pan mechanism provides a panning range of 120 degrees.

Figure 2:
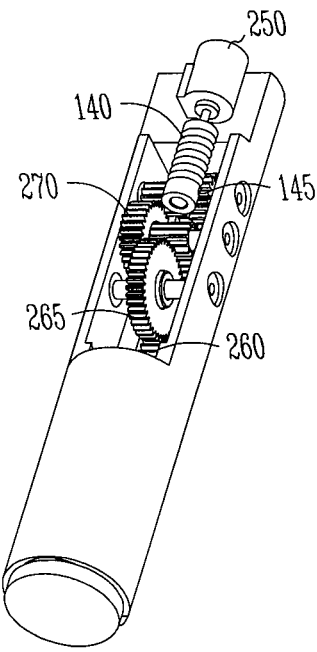
FIG. 2 shows another view of the body-insertable surgical imaging device of FIG. 1.
Figure 2:
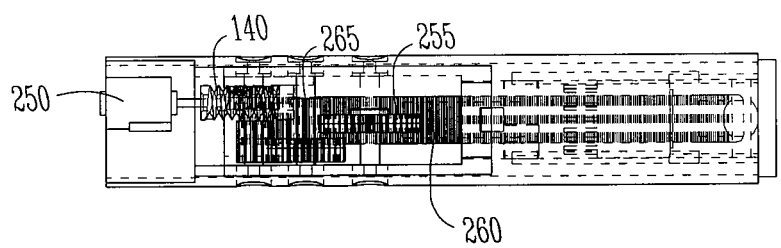
Figure 2:
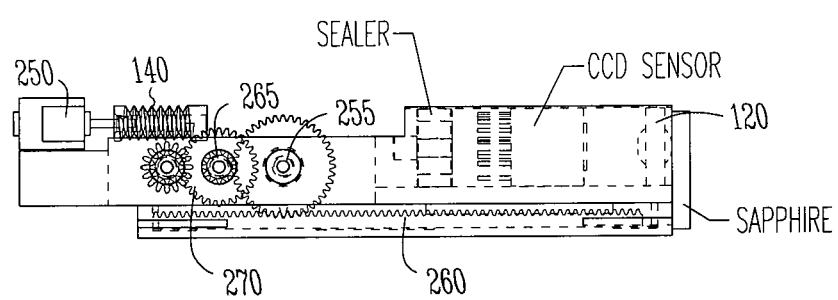

FIG. 2 shows another view of the body-insertable surgical imaging device 100. In some examples, the zoom mechanism can include a rack and pinion mechanism, such as to manipulate the imaging device along the zoom direction. The zoom direction extends from the distal end of the implantable camera 105. In FIG. 1, the zoom direction is along the elongated axis 102. However, when the implantable camera 105 is panned out of elongated axis 102, the zoom direction extends from the distal end of the camera 105 when in the panned position. A stepper motor 250 can be configured to engage and drive a pinion gear of the rack and pinion mechanism. In some examples, three sets of gears can be used in the rack and pinion mechanism, such as to increase or maximize output torque. In some examples, the first gear 255 can include a spur gear. In certain examples, the spur gear can include a 120 diametrical pitch and about forty gear teeth. The first gear 255 can rotate on the rack 260 of the rack and pinion mechanism. In certain examples, the rack 260 can be mounted on a support attached to the external implantable housing. A pinion gear 265 can engage the first gear. When the stepper motor 250 rotates, the pinion gear 265 travels along the rack 260 to move the implantable camera 105 forward and backward along the implantable housing. A second gear 270 can be mounted on the same shaft as the pinion gear 265. In certain examples, the pinion gear can include a 120 diametrical pitch and a number of gear teeth to match the first gear 255 and second gear 270. Such a pinion gear can be mounted on the same shaft as the worm 140. The worm 140 can be mounted on the shaft of the stepper motor 250.

Returning to FIG. 1, in some examples the implantable camera 105 can include an integrated light source 125. In certain examples, the light source 125 light emitting diode (LED). In certain examples, the light source can include multiple LEDs. The multiple LEDs can be mounted on a circular printed circuit board (PCB) and serially connected. In an example, the light source can include eight LEDs. The eight LEDs can be mounted on a PCB having a size of nine millimeters (9 mm) in external diameter, 5 mm in internal diameter, and 3 mm in thickness. In an example, the LEDs are arranged around a lens if the implantable camera 105. In some examples, the control interface 107 can receive a signal (e.g., in response to a user input) to change the light intensity of the light source 125. The control interface 107 adjusts an intensity of the light source 125 in response to the control signal. In some examples, the intensity of the light source 125 is proportional to a voltage, and the received control signal includes a voltage signal to adjust the light intensity.

Figure 3:
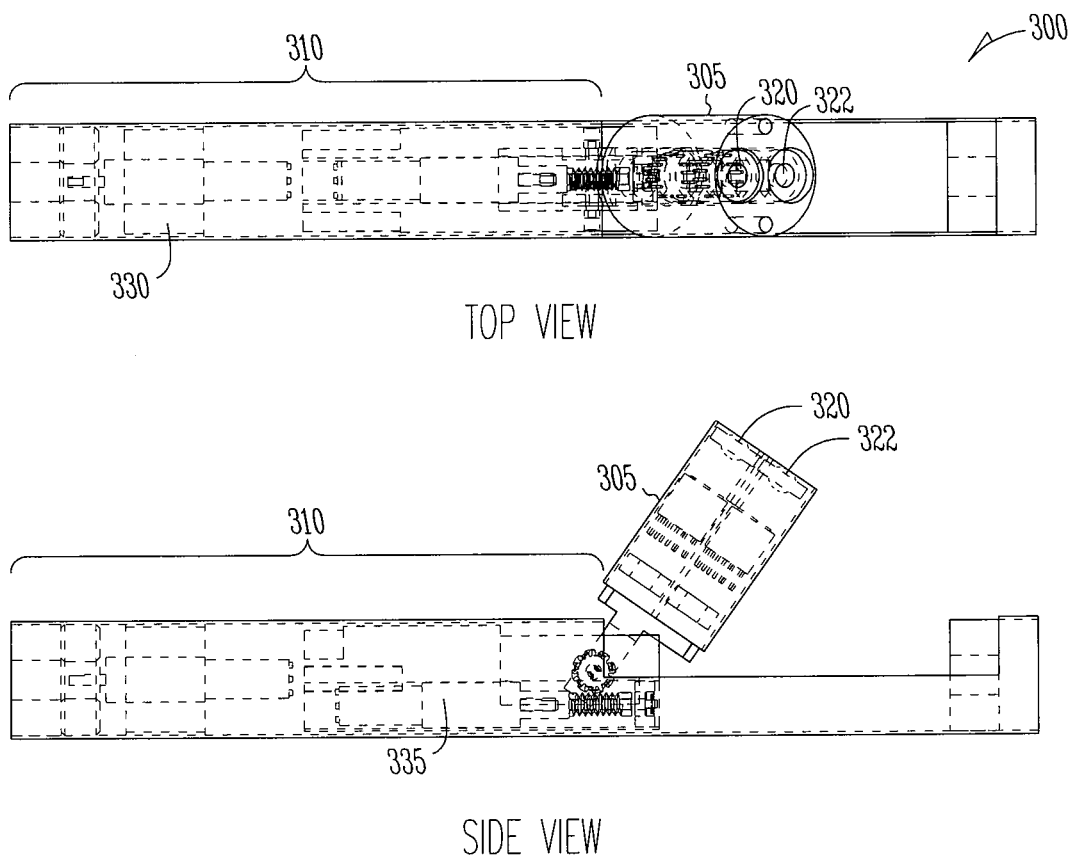
FIG. 3 shows drawings of another example of a body-insertable surgical imaging device.

The use of a stereoscopic or stereo camera having multiple imaging devices and a 3D display in minimally invasive surgery can help compensate for the loss of 3D depth visualization. FIG. 3 shows drawings of another example of a body-insertable surgical imaging device 300. In this example, the imaging device 300 can include an implantable stereo camera 305 and an actuator 310. The implantable stereo camera 305 can include a first camera having a first lens 320 to pass incident light onto a first image sensor (as in the imaging device 100 of FIG. 1), and include a second camera having a second lens 322 to pass incident light onto a second image sensor. In some examples, both image sensors are contained within a single implantable camera housing. In certain examples, the image sensors can include CCD sensors. In certain examples, the image sensors can include CMOS image sensors. The first and second image sensors can be configured to independently generate image data suitable to construct a three-dimension (3D) image. In some examples, the imaging device 300 can include an integrated light source.

The actuator 310 can include a tilt motor 330 and a pan motor 335. In some examples, the actuator 310 includes the zoom mechanism described above. The imaging device 300 can also include a control interface (not shown). Receiving a remotely generated control signal via the control interface allows the stereo camera to be manipulated about a pan axis and a tilt axis in response to the control signal while the camera 305 and actuator 310 are within a body cavity. In some examples, the control interface can receive one or more control signals, such as from a remotely coupled joystick controller. After the surgeon inserts and anchors the imaging device 300 onto the abdomen wall inside the body, he or she can pan and tilt (and in some examples zoom) the stereo camera to the desired surgical viewpoint. In some examples, the motion can be in response to signals received from a remote control device, such as by using simple joystick control. The imaging device 300 can have a modular component design that can be easily disassembled and maintained.

In some examples, the enclosure for the stereo camera can include a cylindrical plastic (Delrin) shell structure. The external diameter of the camera enclosure can be about 15 mm and the length can be about 25 mm. The diameter can allow the stereo camera to be inserted into a 15 mm trocar. In certain examples, the implantable housing for the actuator 310 can include stainless steel. In certain examples, the total length of the imaging device 300 can be about 120 mm.

Figure 4:
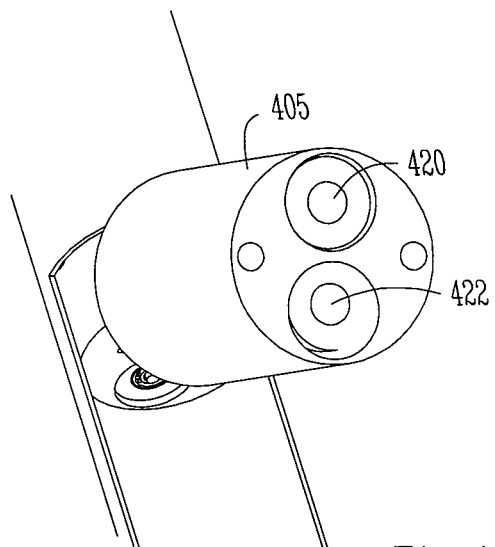
FIG. 4 shows an example of mounting two lenses for a body-insertable stereo camera.

In some examples, the inter-pupillary distance (IPD) of the first lens 320 and the second lens 322 can be less than or equal to one-half the housing diameter. An example of mounting the two lenses for a stereo camera 405 is shown in FIG. 4. In an example of a 15 mm diameter device, two holes each with 6.5 mm in diameter were precisely aligned and drilled with the holes centered a distance of 7 mm apart to accommodate the lenses. This is the IPD for the lenses 420, 422 of the stereo camera 405. Each hole is used to host a lens (e.g., a PTS 5.0 pin-hole lens).

A lens is fixed to the front side of the hole, such as by using glue for example. An image sensor (e.g., a CCD sensor) is inserted into the hole and fixed by a set screw (0-80) after adjusting the focal plane (the view distance was set as 60 mm). In some examples, each image sensor has active pixels of 725(H)×582(V) using the PAL (phase alternating line) video system format, which can provide 450 television (TV) lines in horizontal resolution and 420 TV lines in vertical resolution. Two semicircular parts tightly clamp the end of an image sensor camera head wire. This design packages the fragile soldering point of the sensor and insulates the terminator of the head. A sapphire (e.g., 9.5 mm) is placed in front of lens and sealed, such as by epoxy glue.

Figure 5:
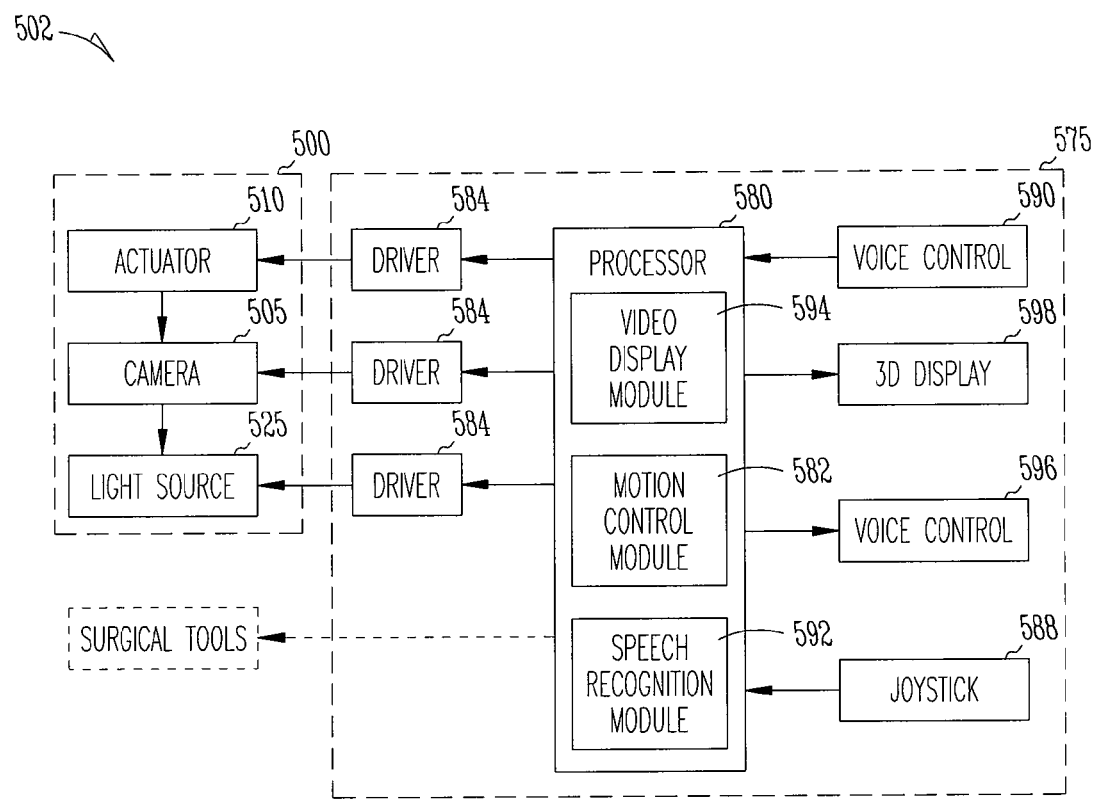
FIG. 5 is a block diagram of an example of an imaging system that includes a body-insertable surgical imaging device and a remote control device.

FIG. 5 is a block diagram of an example of an imaging system 502 that includes a body-insertable surgical imaging device 500 and a remote control device 575. The imaging device 500 includes an implantable camera 505 and an actuator 510. The imaging device 500 can further include a light source 525 integral to the imaging device 500. The camera 505 can include a first image sensor, and a first lens arranged to pass incident light onto the first image sensor.

The actuator 510 can be communicatively coupled to a first control interface to electrically communicate with the external remote control device 575. The actuator 510 supports the camera and manipulates the camera 505 about a pan and tilt axis, when the actuator and camera are inserted in a body cavity, in response to control signal remotely generated at the remote control device 575. In some examples, the actuator 510 includes a zoom mechanism, and the actuator 510 also manipulates the camera 505 in a forward and backward zoom direction in response to a control signal. In some examples, the imaging device 500 adjusts the intensity of the light source 525 in response to a control signal from the remote control device 575.

The remote control device 575 includes a computer 580 and a second control interface (not shown). The computer 580 can include a processor such as a microprocessor (e.g., Intel Pentium III, 863 MHz, with 384 MB RAM), a digital signal processor, application specific integrated circuit (ASIC), or other type of processor, interpreting or executing instructions in software or firmware. The computer 580 can include one or more device drivers 584, such as to communicate with the camera 505, actuator 510, and light source 525.

Functions of the computer 580 are performed by modules. Modules can be hardware, software, or firmware, or combinations of hardware, software, and firmware. Multiple functions can be performed by one or more modules. In some examples, the computer 580 can include a motion control module 582. The motion control module 582 can generate one or more control signals, such as in response to input received via the second control interface. In certain examples, the motion control module 582 can include software executable by the processor. In certain examples, the motion control module 582 can include hardware separate from the processor.

An example of a motion control module 582 can include a National Instruments NIDAQ PCI-6713 control board with a SCB 68 break-out board, which can control one or all of the tilt, pan, and zoom motors' direction, position and velocity. The NIDAQ board can generate a signal that can include a series of control square waves that can be provided to one or more motor drivers (e.g., BLCPS.0002.8, Smoovy, Inc.), which can output an appropriate sequence current to the motor coils to drive the motors at certain speeds. Changing the pulse frequency or shape of a control square wave can provide precise control of the velocity and position of the motors.

In an example, the maximum motor speed can be 15,000 rpm. For the tilt motor, a 625:1 gear ratio head can be used, such as to reduce the speed and increase the motor's torque. For the pan motor, a 125:1 gear ratio head can be installed and connected with a worm gear mechanism having a 16:1 ratio. Therefore, in this example, the speed range for the tilt motor can be from 0 to 24 rpm. In this example, the pan motion can achieve a maximum speed of 0.79 rad/sec.

In some examples, the imaging system 502 can include controller such as a joystick 588 that can be communicatively coupled to the motion control module 582, which can receive input, via the second control interface, from a joystick controller. In certain examples, the computer 580 can include software to poll the aileron and elevator position of the control joystick, and to use these parameters to control the pan and tilt motor's velocity, making for a very easy-to-use and efficient control interface.

In some examples, the motion control device 575 includes an RF receiver or transceiver circuit and the interface between the controller and the computer 580 is wireless. In some examples, the body-insertable imaging device 500 and the motion control device 575 include RF transceivers and the interface between one or more of the drivers 584 and the body-insertable imaging device 500 is wireless. In some examples, the body-insertable imaging device 500 includes a separate power source from the motion control device 575. In this way, the body-insertable imaging device can be physically decoupled from one or more of the controller and the motion control device.

In some examples, the imaging system 502 can include a voice control module 590. The computer 580 can receive input from a microphone. The computer 580 can include a speech recognition module 592 such as to detect voice commands from the signal received from the voice control module 590. The voice commands can be converted into control signals to be sent to the actuator 510.

The computer 580 can receive image data from the implantable camera 505. In some examples, the computer 580 can include a video display module 594 such as to convert image data (received from the first image sensor) to video data, such as for display on a two-dimensional (2D) video monitor 596.

In some examples, the imaging device 500 can include a second camera having a second image sensor, and a second lens, such as to pass incident light onto the second image sensor such as shown in FIG. 3. In an example, the first and second image sensors can independently provide image data to the computer 580 that is suitable to construct a 3D image. In some examples, the processor of the computer 580 is configured to rotate received image data to construct a rotatable 3D image. In certain examples, the 3D image is zoomable through manipulation of the zoom actuator.

In some examples, the imaging system 502 can include a 3D display 598, which can be communicatively coupled to the computer 580. The 3D display 598 can include a first projector, such as to display image date received from the first image sensor, and a second projector, such as to concurrently display image data received from the second image sensor. In some examples, the dual projectors can rear-project the two images from the stereo camera onto a stereo viewing device.

In certain examples, the stereo viewing device can include a display screen, such as a mobile display screen provided on a movable cart. The 3D image can be viewed on the screen, such as by using passive polarized glasses to restrict each image to being viewed by only a single eye. In some examples, the stereo viewing device includes a head-mounted display for providing an image to each eye.

According to some examples, the motion control module 582 of the computer 580 is able to track objects in the image data. The motion control module 582 generates a control signal as the object is moved to manipulate the stereo camera to track the object moved through the 3D image.

In some examples, the motion control module 582 tracks objects by tracking a color centroid of an area in the image that is colored differently from the image background. The tracking is initialized by specifying coordinates of a pixel inside the image area of the object to be tracked. Using the mean red, green, and blue (RGB) values of the region surrounding this starting pixel as a base, the motion control module 582 scans an image neighborhood around the base coordinates to identify pixels having RGB values that are within a specified range of the base RGB values. The mean of the coordinates of these identified pixels are used to identify the centroid to be tracked. The mean RGB values of these identified pixels are used as the base for the next image frame of the iterative tracking process. Using the mean RGB values can improve tracking as lighting changes in the image.

By repeating the scanning process for each image frame, the colored centroid is tracked as it moves in the image. In some examples, tracking parameters such as the size of the neighborhood to be scanned and the acceptable RGB value range (used to identify pixels) are changeable. The values of the parameters generally depend on the object to be tracked. The designated centroid is tracked by each camera in real time. The tracked object is displayed in the 3D image using triangulation of the image points of the object in the individual cameras.

Figure 6:
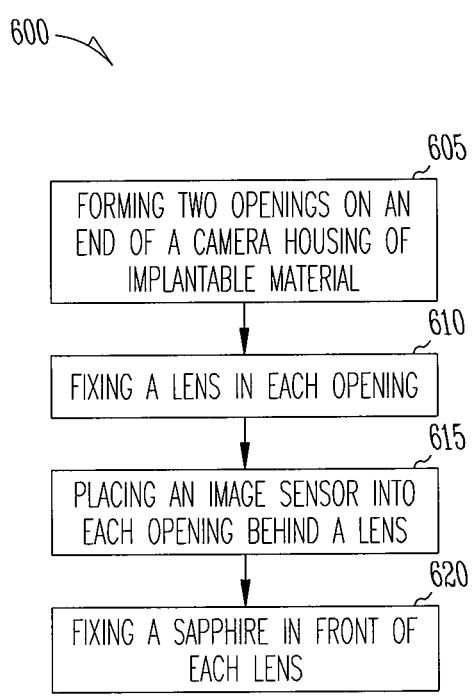
FIG. 6 shows a diagram of a method of making a body-insertable stereo camera.

FIG. 6 shows a diagram of an example of a method 600 of making a body-insertable stereo camera. At 605, two openings can be formed on end of a cylinder-shaped shell of biocompatible material. In certain examples the biocompatible material can include stainless steel. In certain examples, the biocompatible material can include a plastic such as Delrin. In certain examples, the openings can be circular, such as shown in FIG. 4. The center of the openings can be set apart by a distance that defines the inter-pupillary distance (IPD) of the stereo camera. In some examples, the IPD can be about one half the diameter of the cylinder. In an example, the diameter of the cylinder can be about 15 mm and the centers of the openings can be about 7 mm apart.

At 610, a lens can be fixed into each opening. In some examples, the lenses can be sealed to the openings, such as by using glue. In an example, the lenses are miniature pin-hole lenses that can have an F No. of 5.0. In some examples, the lenses can have one or more optical characteristics to provide a view distance (e.g., the distance between the lens and the image object) of 40 mm to 100 mm, and a view angle of fifty degrees.

At 615, an image sensor (e.g., a CCD sensor) can be placed into each opening behind a lens. In certain examples, an image sensor can be fixed in position by a set screw. In certain examples, the set screw can be used to set the view distance. In certain examples, the active area of the image sensor can be a circle (e.g., a circle with a diameter of 4.5 mm). In some examples, a strain relief for head wires connected to the image sensors can be added, such as internal to the housing. The strain relief can provide support for the soldering point of the image sensors and can be an insulator to electrically insulate the terminator of the image sensor heads from the housing if stainless steel is used.

In some examples, the method 600 includes fixing a sapphire in front of each lens at block 620. In certain examples, a sapphire can be sealed to the front of the lens with epoxy glue. In certain examples, a sapphire can be a half ball lens having a diameter of 9.5 mm.

In some examples, the method 600 can include attaching the stereo camera to an actuator that can be movable about a pan axis and a tilt axis. The actuator can provide support for the stereo camera and can allow the stereo camera to be manipulated about the pan and tilt axes while the stereo camera and actuator are inserted into a body cavity. In some examples, attaching the stereo camera to an actuator can include attaching the stereo camera to an actuator movable about a pan axis, a tilt axis, and along a zoom direction.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a body-insertable imaging device including a stereo camera, the stereo camera comprising:
      a first image sensor and a second image sensor within a shared implantable housing having a first lens opening and a second lens opening;
      a first lens configured to pass incident light onto the first image sensor and a second lens configured to pass incident light onto the second image sensor;
   a control interface configured to receive a remotely generated control signal; and
   a body-insertable actuator communicatively coupled to the control interface and configured to support the stereo camera and to be activated by the remotely generated control signal to manipulate the stereo camera and shared implantable housing including rotation about a pan axis orthogonal to the imaging device, rotation about a tilt axis having a direction of an elongated axis of the imaging device, and movement along a zoom direction in response to the control signal while the stereo camera and actuator are within a body cavity, wherein the zoom direction extends from a camera end of the body-insertable stereo camera.

2. The apparatus of claim 1, wherein the actuator includes:
   a pan actuator including a pan motor to manipulate the camera about the pan axis; and
   a tilt actuator including a tilt motor to manipulate the camera about the tilt axis.

3. The apparatus of claim 1, wherein the actuator includes a zoom actuator to manipulate the camera along the zoom direction.

4. The apparatus of claim 3, wherein the zoom actuator includes:
   a rack and pinion mechanism configured to manipulate the imaging device along the zoom direction; and
   a stepper motor configured to engage and drive a pinion gear of the rack and pinion mechanism.

5. The apparatus of claim 1,
   wherein the first and second image sensors are configured to independently generate image data suitable to construct a three-dimensional (3D) image.

6. The apparatus of claim 1, wherein the imaging device includes a light source, wherein the control interface is configured to adjust an intensity of the light source in response to the control signal.

7. The imaging device of claim 1, wherein the control interface includes an RF transceiver configured to receive a remotely generated wireless control signal.

8. The apparatus of claim 1, including a remote control device, wherein the remote control device includes:
   a processor configured to receive image data from the body-insertable imaging device; and
   a second control interface communicatively coupled to the processor, wherein the processor is communicatively coupled to a motion control module configured to generate the control signal in response to input received via the second control interface.

9. The apparatus of claim 8, wherein the processor is configured to receive input from a joystick controller.

10. The apparatus of claim 8, wherein the processor is configured to receive input from a microphone, and
    wherein the processor includes a speech recognition module configured to detect voice commands.

11. The apparatus of claim 8, wherein the body-insertable imaging device includes a second camera sharing the housing with the first camera, wherein the second camera comprises a second image sensor and a second lens configured to pass incident light onto the second image sensor, and wherein the first and second image sensors are configured to independently provide image data to the processor suitable to construct a three-dimensional (3D) image.

12. The apparatus of claim 11, including a 3D display communicatively coupled to the processor, wherein the 3D display includes a first projector configured to display image date received from the first image sensor and a second projector to concurrently display image data received from the second image sensor.

13. The apparatus of claim 11, wherein the motion control module is configured to track objects in the 3D image.

14. The apparatus of claim 11, wherein the motion control module is configured to identify image data and track the image data in the 3D image.

15. The imaging device of claim 11, wherein the processor is configured to rotate the image data in the 3D image.

16. The apparatus of claim 8, wherein the first image sensor includes at least one of a charge coupled device (CCD) sensor and a CMOS sensor, and
wherein the processor includes a video display module configured to convert image data received from the first image sensor to video data for display on a two-dimensional (2D) video monitor.

17. An imaging device comprising:
a light source;
a body-insertable stereo camera, comprising:
    a first image sensor and a second image sensor within a shared implantable housing having a first lens opening and a second lens opening;
    a first lens configured to pass incident light onto the first image sensor and a second lens configured to pass incident light onto the second image sensor, wherein the first and second image sensors are configured to independently provide image data to an external device for constructing a three-dimensional (3D) image;
a control interface configured to receive a remotely generated control signal; and
a body-insertable actuator communicatively coupled to the control interface and configured to support the stereo camera and to be activated by the remotely generated control signal to manipulate the stereo camera and the shared implantable housing, including rotation about a pan axis orthogonal to the imaging device, rotation about a tilt axis having a direction of an elongated axis of the imaging device, and movement along a zoom direction in response to the control signal while the stereo camera and actuator are within a body cavity, including manipulate the stereo camera and the shared implantable housing along the zoom direction while the stereo camera is in a panned position, wherein the zoom direction extends from a camera end of the body-insertable stereo camera.

18. The imaging device of claim 17, wherein the actuator includes:
    a tilt mechanism including a tilt actuator to manipulate the stereo camera about the tilt axis; and
    a pan mechanism including a pan actuator to manipulate the stereo camera about the pan axis.

19. The imaging device of claim 18, wherein the actuator includes a zoom mechanism including a zoom actuator to manipulate the stereo camera along the zoom direction, wherein the zoom direction extends out from a distal end of the stereo camera.

20. The imaging device of claim 19, wherein the zoom mechanism includes:
    a rack and pinion mechanism configured to manipulate the imaging device forward and backward along a zoom direction; and
    a stepper motor configured to engage and drive a pinion gear of the rack and pinion mechanism.

21. The imaging device of claim 17, wherein the light source includes at least one light emitting diode (LED), and wherein the control interface is configured to adjust an intensity of the light source in response to the control signal.

22. The imaging device of claim 17, wherein the control interface is configured to receive the control signal from a joystick controller.

23. The imaging device of claim 17, wherein the control interface includes an RF transceiver and is configured to wirelessly receive the control signal from the joystick controller.

24. A method of making a stereo camera for a body-insertable imaging device, comprising:
    forming two openings on an end of a shared lens housing of implantable material;
    fixing a lens in each opening;
    placing an image sensor into each opening of the shared lens housing behind a lens; and
    attaching the stereo camera and shared lens housing to an actuator movable about a pan axis orthogonal to the imaging device and a tilt axis having a direction of an elongated axis of the imaging device and along a zoom direction when the stereo camera, shared lens housing, and the actuator are inserted into a body cavity, wherein the zoom direction extends from a camera end of the body-insertable stereo camera.

25. The method of claim 24, including fixing a sapphire in front of each lens.

26. The method of claim 25, wherein fixing a lens in each opening includes fixing a pin-hole lens in each opening, and wherein placing an image sensor includes placing a CCD sensor into each opening behind a pin hole lens.

27. The method of claim 24, wherein attaching the stereo camera to an actuator includes attaching the stereo camera to an actuator movable about a pan axis, a tilt axis, and along a zoom direction, wherein the zoom direction extends from a distal end of the stereo camera.

* * * * *